(12) United States Patent
Cattelan et al.

(10) Patent No.: US 8,405,830 B2
(45) Date of Patent: Mar. 26, 2013

(54) DEVICE AND METHOD FOR TAKING SPECTROSCOPIC POLARIMETRIC MEASUREMENTS IN THE VISIBLE AND NEAR-INFRARED RANGES

(75) Inventors: Denis Cattelan, Antony (FR); Enric Garcia-Caurel, Paris (FR); Antonello De Martino, Massy (FR); Bernard Drevillon, Clamart (FR)

(73) Assignees: HORIBA Jobin Yvon SAS, Longjumeau (FR); Centre National de la Recherche Scientifique, Paris (FR); Ecole Polytechnique, Palaiseau (FR)

( * ) Notice: Subject to any disclaimer, the term of this patent is extended or adjusted under 35 U.S.C. 154(b) by 196 days.

(21) Appl. No.: 13/126,618

(22) PCT Filed: Oct. 28, 2009

(86) PCT No.: PCT/FR2009/052087
§ 371 (c)(1),
(2), (4) Date: Apr. 28, 2011

(87) PCT Pub. No.: WO2010/049652
PCT Pub. Date: May 6, 2010

(65) Prior Publication Data
US 2011/0205539 A1 Aug. 25, 2011

(30) Foreign Application Priority Data
Oct. 29, 2008 (FR) ...................................... 08 57377

(51) Int. Cl.
*G01J 4/00* (2006.01)
(52) U.S. Cl. ........................................ 356/369; 356/364
(58) Field of Classification Search ........... 356/364–369
See application file for complete search history.

(56) References Cited

U.S. PATENT DOCUMENTS

| 5,706,212 A | 1/1998 | Thompson et al. |
| 6,175,412 B1 | 1/2001 | Drevillon et al. |
| 7,061,613 B1* | 6/2006 | Huang et al. ................. 356/364 |

(Continued)

FOREIGN PATENT DOCUMENTS
WO 2007/071480 A1 6/2007

OTHER PUBLICATIONS

F. Stabo-EEG et al.: "Design and characterization of achromatic 132° retarders in CAF2 and fused silica", Journal of Modern Optics, vol. 55, No. 14, Aug. 10, 2008, pp. 2203-2214, XP8107343 DOI: 10.1080/09500340802082384, abstract p. 2203, paragraph 1- p. 2205, lase paragraph, Cited in ISR.

(Continued)

*Primary Examiner* — Layla Lauchman
(74) *Attorney, Agent, or Firm* — Young & Thompson

(57) ABSTRACT

A spectroscopic polarimetric system of broad spectral range, includes a light source suitable for emitting an incident light beam over a wavelength range, a polarization state generator (PSG), a polarization state analyzer (PSA), and a detector. The PSG and the PSA have respective elements for modulating the polarization of the light beam. The elements of the PSG for modulating polarization are suitable for generating a sequence of m polarization states with m>4 at each measurement wavelength, the elements of the PSA for modulating polarization are suitable for determining a sequence of n polarization states with n>4 for each measurement wavelength, and the detector elements are suitable for acquiring a sequence of N measurements with $16 < N \leq n \times m$ at each wavelength to extract therefrom a polarimetric spectroscopic measurement of the Mueller matrix of the sample. An extended spectroscopic polarimetric measurement method is also described.

18 Claims, 6 Drawing Sheets

U.S. PATENT DOCUMENTS

| | | | |
|---|---|---|---|
| 7,167,241 | B1 | 1/2007 | Johs et al. |
| 7,196,792 | B2 | 3/2007 | Drevillon et al. |
| 7,369,234 | B2 * | 5/2008 | Beaglehole ............... 356/369 |
| 2004/0130717 | A1 | 7/2004 | Drevillon et al. |

OTHER PUBLICATIONS

F. Stabo-EEG et al.: "Well-conditioned multiple laser Mueller matrix ellipsometer" Optical Engineering, vol. 47, No. 7, Jul. 1, 2008, pp. 073604-1-073604-9, XP40447767, abstract, pp. 073604-1, right-hand column, last paragraph-pp. 073604-3, right-hand column, line 1, Cited in ISR.

Ladstein J. et al.: "Characterisation of liquid crystals for broadband optimal design of Mueller matrix ellipsometers", Proceedings of the Spie—The International Society for Optical Engineering Spie—The international Society for Optical Engineering USA, vol. 6587, May 4, 2007, pp. 65870D-1, XP002532846, ISSN: 0277-786X, Cited in ISR.

De Martiono, et al.: "General methods for optimized design and calibration of Mueller polarimeters", Thin Solid Films, vol. 445-456, 2004, pp. 112-119, XP002532847 DOI: 10.1016/J. tsf.2003.12.052, Cited in ISR.

Tyo J. S.: "Design of optimal polarimeters: maximization of signal-to-noise ration and minimization of systematic error", Applied Optics, OSA, Optical Society of America, Washington, DC, vol. 41, No. 4, Feb. 1, 2002, pp. 619-630, XP002247808, ISSN: 0003-6935, Cited in ISR.

Garcia-Caurel, E. et al.: "Spectroscopic Mueller polarimeter based on liquid crystal devices" Thin Solid Films, vol. 455-456, 2004, pp. 120-123, XP002532848, Cited in ISR.

International Search Report, dated Feb. 2, 2010, from corresponding PCT application.

* cited by examiner

DEVICE AND METHOD FOR TAKING SPECTROSCOPIC POLARIMETRIC MEASUREMENTS IN THE VISIBLE AND NEAR-INFRARED RANGES

The present invention relates to a spectroscopic Mueller matrix ellipsometer (MME) and/or polarimeter improved to operate over a broad range of wavelengths with good quality measurement.

More particularly, the spectroscopic ellipsometer or polarimeter of the present invention operates over a broad spectral range covering the visible and the near infrared (350 nanometers (nm) to 2 micrometers (μm)) and it presents good conditioning over this broad spectral range. The invention preferably relates to a polarimeter using liquid crystal (LC) devices for modulating the polarization states of light.

Spectroscopic Mueller ellipsometers and polarimeters that operate in the visible range already exist. Such devices serve at each wavelength of the spectrum to measure 16 Mueller matrix coefficients that are characteristic of a sample. The Mueller matrix is generally represented in the form of a matrix M of dimension 4×4. US patent No. 2004/0130717 in the name of Drévillon et al. describes a polarimetric system based on liquid crystal cells. That system comprises an excitation portion and a detection portion. The excitation portion emits a light beam that is transmitted by a polarization state generator (PSG) and is then reflected or transmitted by a sample. The beam as reflected or transmitted by the sample passes through the detection portion that comprises a polarization state analyzer (PSA) and a detector. The PSG and the PSA are symmetrical, each comprising a linear polarizer and two liquid crystal cells based either on ferroelectric crystals or on nematic crystals. A conventional complete measurement consists in making 16 acquisitions by modulating the polarization of the light in the PSG and in the PSA. The modulation of polarization in the liquid crystal devices is controlled electrically by causing the voltage applied to each liquid crystal to vary sequentially between two values $V_A$, $V_B$, in such a manner as to modulate the polarization state of the light at the outlet from each LC between two states A and B. The liquid crystal devices, regardless of whether they are nematic or ferroelectric, behave like retardation or "delay" plates that are characterized by the orientations of their optical axes, and also by the phase shifts created between two perpendicular components of the electric field associated with the light beam passing therethrough. For ferroelectric crystals (FLC), the phase shift remains constant regardless of the applied voltage, but the orientation of the optical axis switches between two respective stable positions $\theta_A$ and $\theta_B$. FLCs are bistable elements. In contrast, for a nematic crystal (NLC), the orientation of its optical axis remains constant, but the induced phase shift varies continuously and non-linearly as a function of the applied voltage V. Applying two voltages $V_A$ and $V_B$ thus generates two different delays.

A conventional polarimeter operating by using the smallest number of polarization states for measuring a complete Mueller matrix is generally configured to make 16 measurements. The PSG of such a polarimeter generates four polarization states corresponding to four Stokes vectors, and the PSA analyzes four polarization states corresponding to four Stokes vectors. The PSG is represented by a modulation matrix W of dimension 4×4 and the PSA by a modulation matrix A of dimension 4×4.

This applies in particular to ferroelectric liquid crystal polarimeters having two liquid crystal devices in the PSG and two liquid crystal devices in the polarization state analyzer. Each liquid crystal device may be controlled by electronics for switching between two polarization states. In similar manner, a nematic liquid crystal polarimeter is controlled to apply two voltage values so that each nematic liquid crystal device generates two delays and thus two polarization states.

Regardless of the type of liquid crystal used (FLC or NLC), the acquisition and the processing of a sequence of 16 measurements thus serves to fully determine the 16 coefficients of the looked-for Mueller matrix. The PSG is conventionally represented in the form of a (4×4) modulation matrix W in which the columns are the four Stokes vectors generated by the PSG. Similarly, the PSA is represented in the form of a (4×4) demodulation matrix A in which the four rows correspond to the four Stokes vectors analyzed by the PSA. The sequence of 16 measurements may be represented in the form of a (4×4) matrix S defined as follows:

$$S = A \cdot M \cdot W \quad (1)$$

In certain circumstances, inverting this equation makes it possible to determine the Mueller matrix of the sample:

$$M = A^{-1} \cdot S \cdot W^{-1} \quad (2)$$

Nevertheless, the inversion operation is not always possible. It is impossible when A and W are singular, since it is not possible to define an inverse matrix for such matrices. There are also matrices that, even though they are not singular, are nevertheless very similar to singular matrices. From a numerical point of view, inverting such matrices is very unstable and gives rise to large calculation errors. One of the postulates of linear algebra stipulates that for any matrix there always exists an associated diagonal matrix for which the non-zero elements are known as the singular values. Singular matrices have one or more zero singular values. Matrices that are similar to singular values have one or more singular values that are very small. In order to evaluate whether a matrix is singular or nearly singular, it is possible to use an indicator referred to as conditioning (C). This indicator may be defined as the ratio between the smallest and the largest of the singular values. In the literature, certain authors use definitions for conditioning that are slightly different from that used in this document. For example, Scott Tyo [J. Scott Tyo, "Design of optimal polarimeters: maximization of signal-to-noise ratio and minimization of systematic error", Applied Optics, 41 (2002), p. 619] uses the ratio between the largest and the smallest of the singular values. In general that definition and other definitions are equivalent, and the conclusions made possible by the definition used in the present document can be reproduced using the other existing definitions.

Another feature of conditioning that makes it advantageous to use, is that the accuracy of measurements at any wavelength depends on the value of the conditioning since the propagation of noise and of errors in the measured matrix S to the calculated matrix M is proportional to 1/C.

For a polarimeter made with perfect linear delays and linear polarizers, the maximum value of the conditioning is ideally equal to $1/\sqrt{3} \approx 0.57$. Such optimum conditioning may be achieved experimentally for a monochromatic polarimeter. Nevertheless, in a spectroscopic polarimeter, conditioning generally varies as a function of wavelength because of the dispersion in the optical components used (lenses, liquid crystal devices, delay plates, . . . ). Nevertheless, a spectroscopic polarimeter may be optimized over a spectral range of wavelengths by adjusting the orientations and/or the phase shifts of the components of the PSG and of the PSA (cf. US 2004/0130717). In order to evaluate the quality of a polarimeter it is possible to take the conditioning value as the criterion. Empirically, it is considered that the conditioning of a spectroscopic polarimeter must in practice lie in the range 0.2 to 0.57 over the entire utilization spectrum. A conditioning value of less than 0.2 makes the values of the Mueller matrix too noisy for them to be usable. The first criterion is thus to avoid having minima less than 0.2 to 0.3 over the entire spectrum. A second assessment criterion is the uniformity of the conditioning over the spectral range under consideration, where this determines the uniformity of measurement accuracy over the entire measurement spectral range.

There thus exist spectroscopic polarimeters for the visible range and others for the near infrared range. By way of example, the publication Ladstein et al. (Phys. Stat. Sol. 5, No 5, pp. 1097-1100, 2008) describes a near infrared polarimeter comprising two ferroelectric liquid crystal devices $LC_1$, $LC_2$ and two fixed delay plates $F_1$, $F_2$ both in the PSG and in the PSA ($LC_2$, $LC_4$ and $F_3$, $F_4$, respectively) (cf. FIG. 1). That device serves to cover the entire near infrared spectral range (800 nm to 1600 nm) with conditioning of satisfactory level and uniformity. Nevertheless, is it observed that the conditioning curves tend to drop off steeply at the ends of the spectral range.

Two polarimeters, one for the visible (400 nm to 800 nm) and the other for the near infrared (800 nm to 1600 nm) are presently needed in order to perform measurements covering the spectral range 400 nm to 1600 nm with good accuracy. At present there does not exist any Mueller polarimeter covering the entire visible to near infrared range with an acceptable and uniform conditioning criterion.

One of the objects of the invention is to propose a polarimeter capable of providing measurements over the spectral range 350 nm to 2000 nm, while presenting conditioning of a level that lies between the limit values (in the range 0.2 to 0.57) and that is relatively uniform.

The present invention provides a spectroscopic polarimetric system for analyzing a sample, the system comprising: an excitation portion that comprises a light source suitable for emitting an incident light beam over a wavelength range and a polarization state generator (PSG) comprising a linear polarizer and means for modulating the polarization of the light beam, an analyzer portion that comprises a polarization state analyzer (PSA) comprising means for modulating the polarization of the light beam and a linear polarizer, and detector means for detecting the light beam as a function of wavelength and including a processor unit. According to the invention, the means for modulating the polarization of the PSG comprise three liquid crystal devices and voltage control means applied to each of the liquid crystal devices suitable for modulating the orientation and/or the delay of the polarization states so as to generate a sequence of $m$ polarization states with m>4 at each measurement wavelength; the means for modulating the polarization of the PSA comprise three liquid crystal devices and voltage control means applied to each of the liquid crystal devices suitable for modulating the orientation and/or the delay of the polarization states so as to determine a sequence of n polarization states with n>4 at each measurement wavelength, and the detector means are suitable for acquiring a sequence of N light intensity measurements where:

$$16 < N \leq n \times m$$

at each wavelength to extract the Mueller matrix of the sample therefrom.

In a particular embodiment, the excitation portion includes a retractable platform situated between the PSG and the sample and suitable for introducing at least one calibration element in the optical system of the polarimetric system and for withdrawing said calibration element once calibration has been terminated, and the analyzer portion includes a retractable platform situated between the PSA and the sample and suitable for introducing at least one calibration element in the optical system and for withdrawing said calibration element once calibration has been terminated.

In a first mode, the means for modulating the polarization of the PSG are suitable for generating a sequence of m=8 polarization states at each measurement wavelength, the means for modulating polarization of the PSA are suitable for determining a sequence of n=8 polarization states at each measurement wavelength, and the detector means are suitable for acquiring a sequence of N=64 measurements at each wavelength to extract the Mueller matrix of the sample therefrom. This mode is referred to below in the present document as "complete mode".

In a second mode, the means for modulating the polarization of the PSG are suitable for generating a sequence of m=6 polarization states at each measurement wavelength, the means for modulating the polarization of the PSA are suitable for determining a sequence of n=6 polarization states at each measurement wavelength, and the detector means are suitable for acquiring a sequence of N=36 measurements at each wavelength to extract the Mueller matrix of the sample therefrom. This mode is referred to below in the present document as "reduced mode".

In an embodiment, the means for modulating the polarization of the PSG comprise three ferroelectric liquid crystal (FLC) devices suitable for generating a sequence of m=8 polarization states, and the means for modulating the polarization of the PSA comprise three FLC devices suitable for determining a sequence of n=8 polarization states.

In another embodiment, the PSG has a delay plate located between two of the ferroelectric liquid crystal devices, and the PSA has a delay plate located between two of the ferroelectric liquid crystal devices.

In a particular embodiment, the delay plates are achromatic double prisms.

In an embodiment, the liquid crystal devices are nematic liquid crystal devices and the polarimetric system includes an electronic control device suitable for modulating the delays of the nematic liquid crystals.

In an embodiment, the polarization modulating means of the PSG and of the PSA respectively comprise three nematic liquid crystal (NLC) devices, and the voltage control means are suitable for switching the delay of each NLC device in such a manner as to generate a sequence of m=8 polarization states and respectively to determine a sequence of n=8 polarization states.

In an embodiment, the polarimetric system is optimized for the spectral range 350 nm to 2 μm.

In an embodiment, the polarimetric system is an ellipsometer.

In an embodiment, the polarimetric system is a polarimeter serving to determine the Mueller matrix of a sample from a sequence of N detected light intensity measurements where N is greater than 16. In the complete mode of operation, N=64, and in the reduced mode of operation, N=36.

In an embodiment, the detector means comprise an imaging detector adapted to the processor unit to form a polarimetric image of the sample.

The invention also provides a method of spectroscopic polarimetric measurement of a sample, the method comprising the following steps:

illuminating the sample by means of an incident light beam coming from a source emitting light in a range of wavelengths. The polarization state of said beam is determined by the PSG comprising a polarizer. Said PSG modulates the polarization state of the light beam, and said sample transmits or reflects the polarization modulated light beam;

detecting the measurement by means of a detector and a detection section comprising a polarization state analyzer and a polarizer, said PSA determining the polarization state of the detected light beam; and processing the detected signals in order to extract a polarimetric measurement of the sample therefrom.

According to the invention, the polarization states generated by three liquid crystal devices are modulated in a sequence of m>4 polarization states, the polarization states analyzed by three liquid crystal devices are determined in a sequence of n>4 polarization states, and a sequence of N=n×m measurements.

In a preferred implementation of the spectroscopic polarimetric measurement method, a sequence of eight polarization states is generated, a sequence of eight polarization states is analyzed, and a sequence of 64 measurements is acquired at each wavelength.

In another implementation of the spectroscopic polarimetric measurement method of the invention, a sequence of six polarization states is generated, a sequence of six polarization states is analyzed, and a sequence of 36 measurements is acquired at each wavelength.

The present invention also relates to the characteristics that appear from the following description and that may be considered in isolation or in any technically feasible combination.

This description is given by way of non-limiting example and serves to make it better understood how the invention can be implemented with reference to the accompanying drawings, in which:

FIG. 1 is a diagram of a liquid crystal polarimeter of the prior art;

FIG. 2 plots conditioning spectral curves for the FIG. 1 polarimeter;

Figure 12:
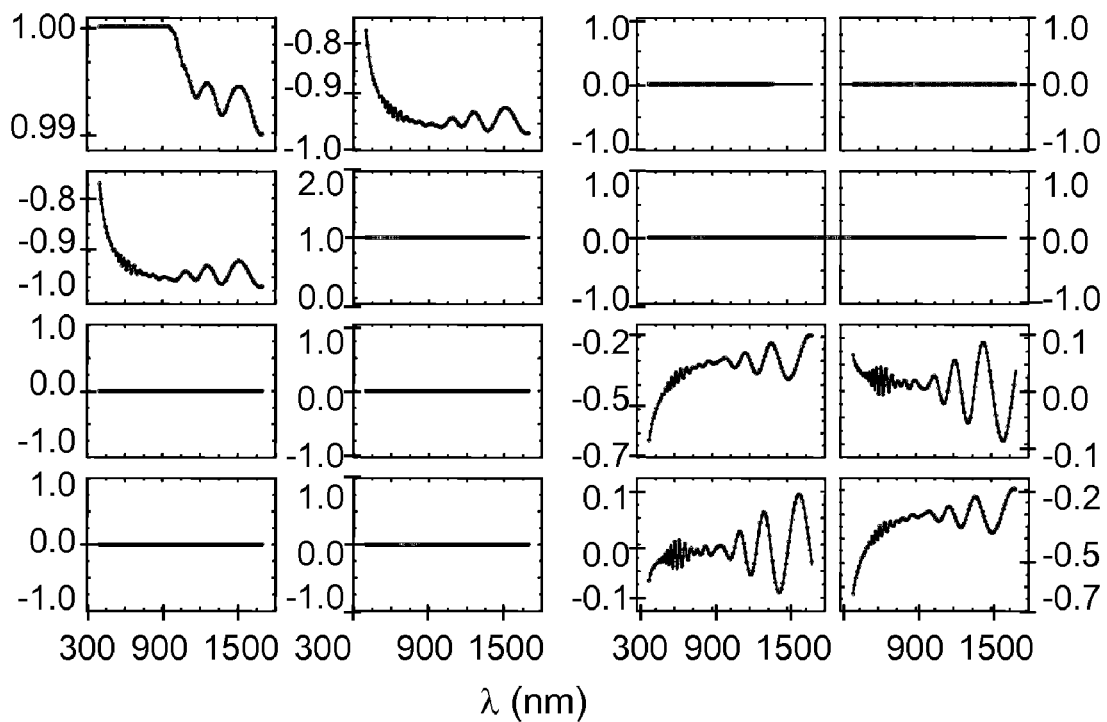
Figure 13:
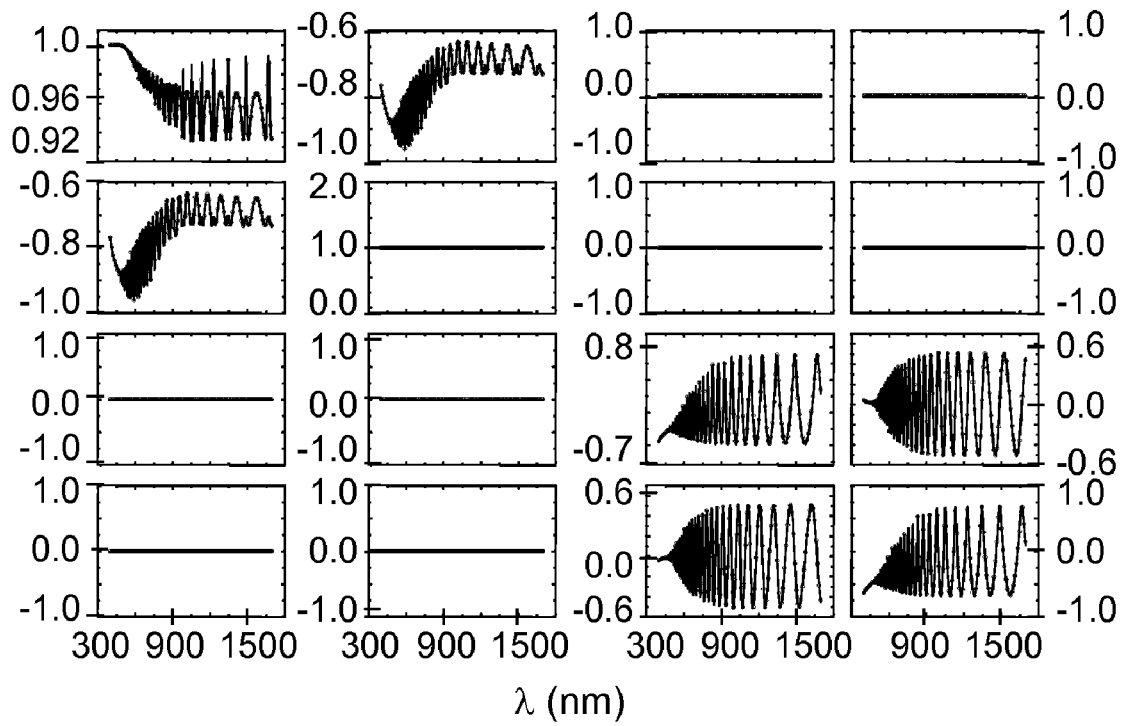

FIG. 12 shows a simulated example of measuring a Mueller matrix in the 400 nm to 1800 nm spectral range for a crystalline silicon wafer covered with a thin layer of monocrystalline silicon (layer having a thickness of 1 micrometer); between the layer and the substrate there is an amorphous silicon interface having a thickness of 20 nm; and FIG. 13 shows a simulated example of measuring a Mueller matrix in the spectral range 400 nm to 1800 nm corresponding to a layer of silicon having a thickness of 2 micrometers on a glass substrate.

Figure 1:
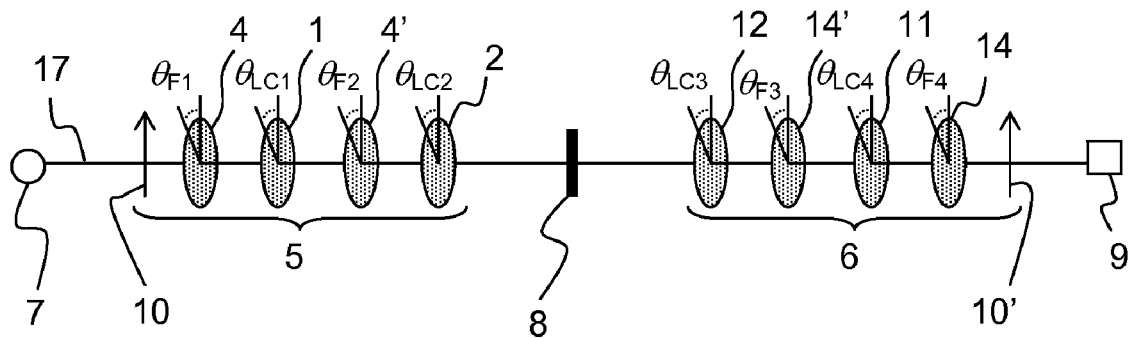

FIG. 1 is a diagram showing the structure of a prior art liquid crystal polarimeter. The polarimeter comprises a light source 7, a polarization state generator (PSG) 5, a polarization state analyzer (PSA) 6, and a detector 9. The PSG 5 comprises a polarizer 10, two liquid crystal devices 1 and 2, and two fixed delay plates 4 and 4'. In symmetrical manner, the PSA 6 comprises two liquid crystal devices 11 and 12, two fixed delay plates 14 and 14', and a polarizer 10'. A light beam 17 emitted by the source 7 is polarization modulated by the polarization state generator, and then illuminates the sample 8. The light beam as reflected or transmitted by the sample is once more polarization modulated by the PSA and reaches the detector 9. The generator 5 comprises two liquid crystals and is capable of generating four polarization states; the same applies to the analyzer 6. A measurement comprises acquiring 16 coefficients, corresponding to a sequence of 16 polarization states of the PSG and of the PSA.

Between the PSG 5 and the sample 8 there is a retractable platform 21 (not shown in FIG. 1) that serves to introduce different calibration samples into the optical system during calibration of the PSG. During routine measurements, this platform withdraws the calibration samples from the optical system. In similar manner, between the sample 8 and the PSA, there is another retractable platform that serves to introduce different calibration samples into the optical system during calibration of the PSA. During routine measurements, this platform withdraws the calibration samples from the optical system.

Figure 2:
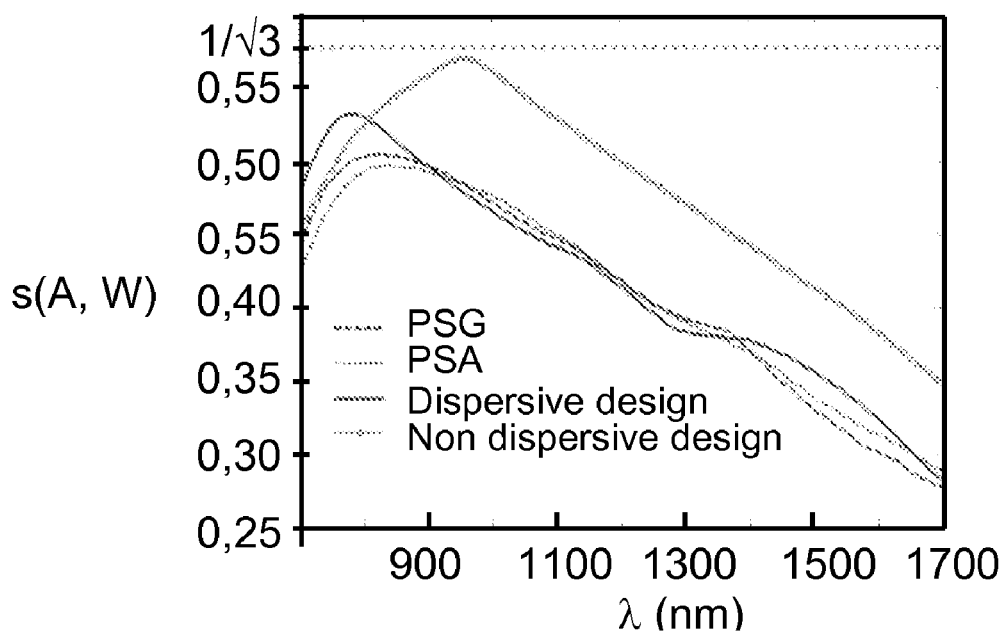

The orientation of the axes of the components, and the phase shifts induced by the fixed delay plates are optimized so that the conditioning criterion is at a maximum over a wide spectral range. The use of achromatic plates 4, 4' makes it possible in certain circumstances to improve the conditioning criterion. Nevertheless, the utilization range nevertheless remains limited to the near infrared (800 nm to 1600 nm), as shown in FIG. 2.

Various configurations of polarimeters are described below in order to illustrate different embodiments of the invention. The performance and the robustness of the various configurations are also described.

The polarization modulation means of the polarimeter of the invention are advantageously ferroelectric liquid crystal (FLC) devices or nematic liquid crystal (NLC) devices. Nevertheless, the invention is not limited to these polarization modulation means.

In a polarimeter of the invention, the PSG generates $\underline{m}$ polarization states corresponding to $\underline{m}$ Stokes vectors, and the PSA analyzes $\underline{n}$ polarization states corresponding to $\underline{n}$ Stokes vectors. The $\overline{PSG}$ is represented by a modulation matrix W of dimension 4×m and the PSA is represented by a modulation matrix A of dimension n×4. As for the above-described polarimeters, the set of N measurements may be grouped together in the form of a matrix, referred to below in this document as the matrix S, which is of dimension n×m. Generalizing equation (1) enables the various elements of the matrix S to be written as follows:

$$S_{p,k} = \sum_{i=1}^{4} \sum_{j=1}^{4} A_{p,i} M_{i,j} W_{j,k} \text{ for } p[1, n]k[1, m]i[1, 4], \text{ and } j[1, 4] \qquad (3)$$

The application of the equation (2) as generalized and adapted to the sizes of the matrices A and W can be written as follows:

$$M_{i,j} = \sum_{p=1}^{n} \sum_{k=1}^{m} A_{i,p}^{-1} S_{p,k} W_{k,j}^{-1} \text{ for } p[1, n], k[1, m], i[1, 4], \text{ and } j[1, 4] \quad (4)$$

This equation (4) enables the Mueller matrix to be extracted from the measurement matrix S, together with the pseudo-inverse matrices $A^{-1}$ and $W^{-1}$ from the matrices A and W respectively. Numerical methods enabling the pseudo-inverse matrices to be calculated are reported by W.H. Press et al. [Numerical recipes in Pascal, Cambridge University Press]. The matrices A and W are determined during calibration of the polarimeter.

The step of calibrating the polarimeter is very tricky. The accuracy and the precision of the measurements provided by the apparatus depend on this calibration step. So far as we know, the present state of the art presents essentially two different strategies for calibrating a polarimeter. The first strategy consists in modeling all of the optical elements making up the optical system of the instrument, one by one. This often implies introducing empirical parameters of values that must subsequently be found by measuring reference samples and by imposing a series of assumptions on the expected measurements. That method, which is the most widespread, presents several drawbacks. Firstly, it is necessary for the apparatus that is to be calibrated to be made up of optical elements that are sufficiently well known and sufficiently stable for them to be capable of being modeled by simple mathematical relationships. Thereafter, it is necessary to have reference samples presenting properties that are sufficiently stable and well known for it to be possible to extrapolate their responses without measuring them. The second strategy is an original method proposed by Drévillon and Compain [U.S. Pat. No. 6,175,412] known as the eigen value method. That method, which is numerically very robust, makes it possible to do without detailed knowledge of the optical responses of the optical elements making up the polarimeter. This advantage makes it possible to use the method for calibrating any type of polarimeter. Given that the behavior of liquid crystals is known in very approximate manner only, in our circumstances we have selected to calibrate the polarimeter using the eigen value method as described by Drévillon and Compain. In the prior art, the eigen value method has already been used by Drévillon and De Martino for calibrating a conventional polarimeter [U.S. Pat. No. 7,196,792]. In our circumstances we apply the same procedure as that described by Drévillon and De Martino.

The generator 5 and the polarization state analyzer 6 described in the following embodiments are advantageously symmetrical, thus making it possible to reduce fabrication costs. Nevertheless it is also possible to envisage non-symmetrical embodiments in the ambit of the invention.

These various configurations are summarized in the table below:

TABLE 1

Examples of configurations

| | Configuration | | | | | |
|---|---|---|---|---|---|---|
| | I | II | III | IV | V | VI |
| Number and type of liquid crystal devices in PSG or PSA | 3 FLC | 3 FLC | 3 FLC + 1 fixed delay wave plate | 3 FLC + 1 fixed delay wave plate | 3 NLC | 3 NLC |
| Generation and acquisition sequence (N) | 64 | 36 | 64 | 36 | 64 | 36 |

Nevertheless, the invention is not limited to these few configurations.

Figure 3:
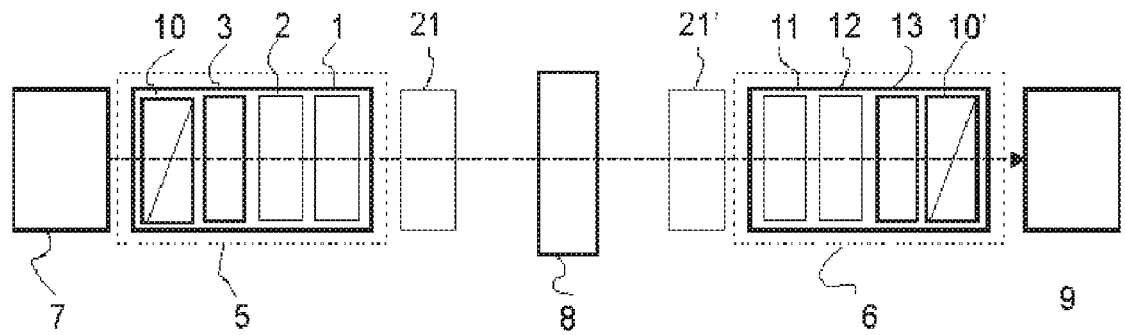
FIG. 3 is a diagram of a first embodiment (types I or II) of a polarimeter of the invention.

In a first embodiment of the invention (config. I), shown diagrammatically in FIG. 3, the polarimeter has a polarization state generator 5 comprising three ferroelectric liquid crystal devices 1, 2, and 3, together with a polarization state analyzer 6 comprising three ferroelectric liquid crystal devices 11, 12, and 13.

Each liquid crystal device (1, 2, 3, 11, 12, 13) is electrically controlled to switch between two stable polarization states, with the phase shift in the two states being identical and the polarization axis of the device switching through ±45°. The two possible polarization states for each device are labeled diagrammatically by the letters A and B.

The polarization state generator 5 is thus suitable for generating a sequence of eight different polarization states:

TABLE 2

Generating a sequence of eight polarization states with three liquid crystal devices

| Polarization state No. | FLC1 | FLC2 | FLC3 |
|---|---|---|---|
| 1 | $A_1$ | $A_2$ | $A_3$ |
| 2 | $A_1$ | $A_2$ | $B_3$ |
| 3 | $A_1$ | $B_2$ | $A_3$ |
| 4 | $A_1$ | $B_2$ | $B_3$ |
| 5 | $B_1$ | $A_2$ | $A_3$ |
| 6 | $B_1$ | $A_2$ | $B_3$ |
| 7 | $B_1$ | $B_2$ | $A_3$ |
| 8 | $B_1$ | $B_2$ | $B_3$ |

Likewise, the polarization state analyzer 6 is suitable for analyzing a sequence of eight polarization states. The polarimeter can thus perform a sequence of sixty-four (N=64) acquisitions corresponding to 64 polarization state combinations of the ferroelectric liquid crystal 1, 2, 3, 11, 12, and 13.

Each ferroelectric liquid crystal device, respectively 1, 2, 3, 11, 12, or 13 is designed to introduce a phase shift of 90° for a specific wavelength λ. The values of these wavelengths that enable the conditioning value to be optimized in the measurement spectroscopic range are given in Table 3. Because of the chromatism of liquid crystals, the phase shift imparted by each device is not equal to 90° at any wavelength other than that specified in the table. The polarization state generator 5 is symmetrical relative to the polarization state analyzer 6. The relative orientations of the devices 1, 2, and 3 are adjusted as set out in Table 3 below, so as to optimize the conditioning value in the measurement spectral range.

TABLE 3

Optimized values for the orientations of the three
FLCs of a PSG and of a PSA in config. I

| $\Delta LC_3 = 90°$ | $\lambda_3 = 1150$ nm | $\theta_3 = 46°$ |
|---|---|---|
| $\Delta LC_2 = 90°$ | $\lambda_3 = 1050$ nm | $\theta_3 = -5°$ |
| $\Delta LC_1 = 90°$ | $\lambda_1 = 600$ nm | $\theta_1 = 72°$ |

Figure 6:
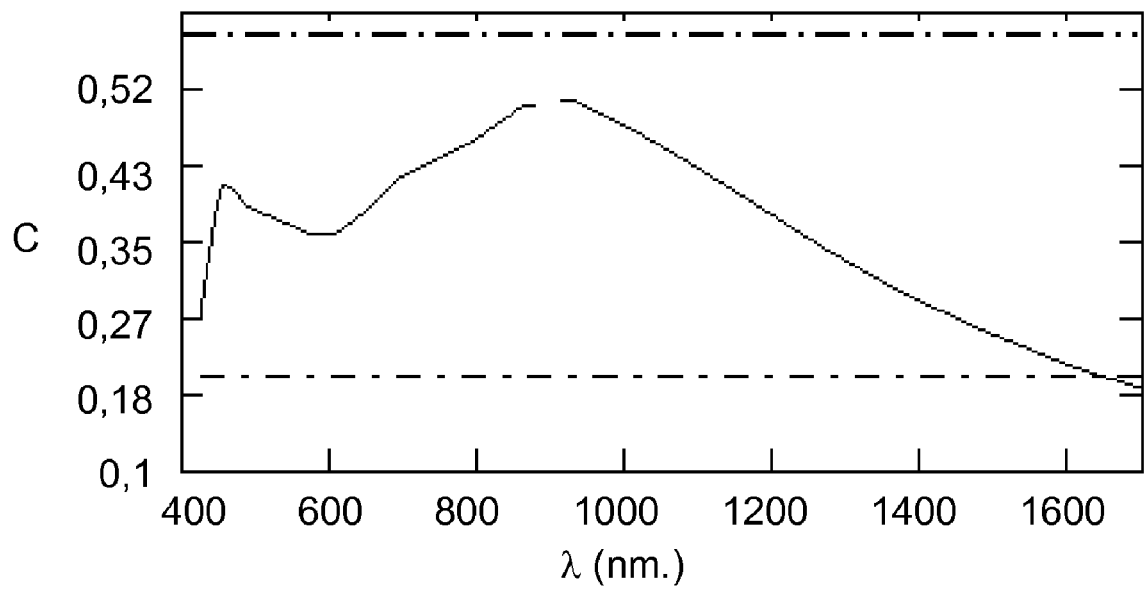
FIG. 6 shows a conditioning spectrum corresponding to a polarimeter of the invention in a type I configuration.

FIG. 6 shows a conditioning spectral curve of a polarimeter in a type I configuration (complete mode) resulting from optimizing the parameters, the delays, and the orientations, of the three liquid crystal devices. The conditioning values obtained are situated in the range 0.2 to 0.51 for a very broad range of wavelengths 420 nm to 1600 nm approximately. This conditioning presents good uniformity over the entire spectral range.

The robustness of each configuration is evaluated for different sources of experimental error: alignment error for the optical axes of the components, temperature drift of the delays, . . . . A map of conditioning curves for delay variations in FLC1, FLC2, and FLC3 is drawn up. The acceptable conditioning limit values provide a tolerance value. Thus, it can be seen that in configuration I (3FLCs, N=64), tolerance on the delay error is ±4° for the FLCs 2 and 3, and ±10° for the FLC1.

Furthermore, this configuration I (complete mode) requires a sequence of 64 acquisitions, instead of a conventional sequence of 16 acquisitions for a prior art polarimeter having 16 polarization states. Acquisition thus takes four times as long. Even if the spectral range accessible using a single polarimeter is considerably enlarged compared with polarimeters of the state of the art, lengthening the duration of acquisition by a factor of four constitutes a drawback.

In a variant of the first embodiment of the invention (config. II or reduced mode), the polarimeter is identical to the polarimeter described above under the name configuration I. This reduced-mode polarimeter shown diagrammatically in FIG. 5 comprises three ferroelectric devices 1, 2, and 3 in the polarization state generator 5, and three respective ferroelectric devices 11, 12, and 13 in the polarization state analyzer 6, and is suitable for generating 64 polarization states. Nevertheless, in this reduced mode, the acquisition system acquires only a sequence of 36 acquisitions selected from the 64 possible acquisitions: the PSG 5 generates a sequence of six polarization states (out of the eight possible in Table 2), and the PSA 6 analyzes only a sequence of six polarization states (out of the eight possible); for example the reduced sequence makes use of polarization states Nos. 1, 2, 3, 4, 6, and 8 (Table 2).

In order to operate the polarimeter in this reduced mode (config. II), the relative orientations of the devices 1, 2, and 3 are adjusted as set out in Table 4 so as to optimize the conditioning spectrum for the six polarization states that are used in the polarization state generator 5 and analyzer 6.

The values obtained are as follows:

TABLE 4

Optimized values for the orientations of three FLCs
in a PSG and a PSA in config. II

| $\Delta LC_3 = 90°$ | $\lambda_3 = 1180$ nm | $\theta_3 = 45.0°$ |
|---|---|---|
| $\Delta LC_2 = 90°$ | $\lambda_3 = 1000$ nm | $\theta_3 = -5.0°$ |
| $\Delta LC_1 = 90°$ | $\lambda_1 = 600$ nm | $\theta_1 = 58°$ |

Figure 7:
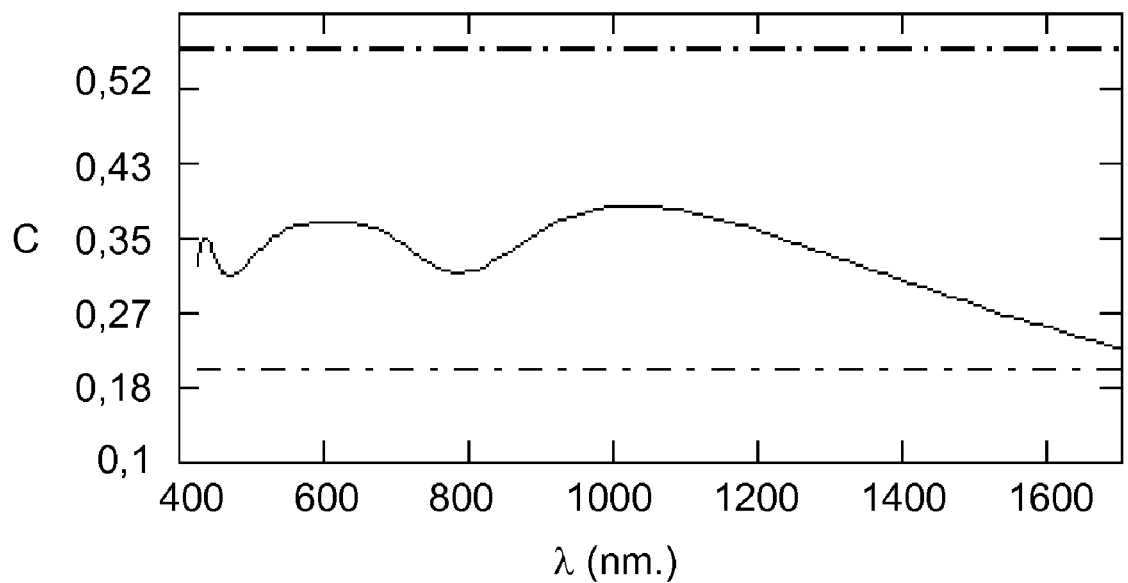
FIG. 7 shows a conditioning spectrum corresponding to a polarimeter of the invention in a type II configuration.

FIG. 7 shows the conditioning values in the spectroscopic range 400 nm to 1700 nm corresponding to a PSG or a PSA mounted in configuration II using the specifications set out in Table 4. The conditioning values obtained lie in the range 0.2 to 0.4. It can be seen that there is a degradation in conditioning compared with that of configuration I (FIG. 6), due to reducing the number of acquisitions form 64 to 36. Nevertheless, the conditioning presents good uniformity (no peaks) over the spectral range. This configuration II has the advantage of lengthening the total duration of acquisition by a factor of about two in comparison with a conventional acquisition using a sequence of 16 polarization states. Nevertheless, this configuration II (reduced mode) is more sensitive than configuration I (complete mode) to alignment errors of the components (tolerance <±3°) and also to delay variations in FLC1 and FLC4 (<±5°). Since drift in delay is often the result of temperature variations, this configuration thus requires good temperature regulation.

Figure 4:
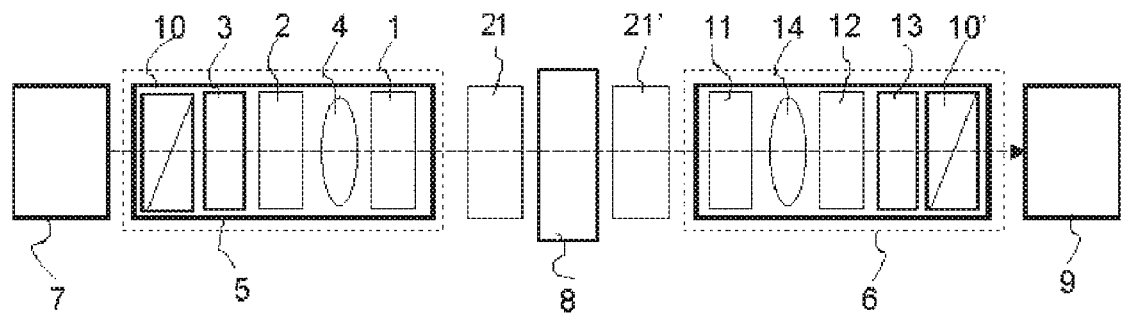
FIG. 4 is a diagram of a second embodiment (types III or IV) of a polarimeter of the invention.

In a second embodiment of the invention (config. III, complete mode), shown diagrammatically in FIG. 4, the polarimeter comprises a PSG 5 having three ferroelectric liquid crystal devices 1, 2, and 3, together with an achromatic half-wave plate 4. The PSA 6 is symmetrical to the PSG 5 and comprises three ferroelectric liquid crystal devices 11, 12, and 13, together with an achromatic half-wave plate.

TABLE 5

Optimized values for the orientations of three FLCs
of a PSG or a PSA in config. III

| $\Delta LC_3 = 90°$ | $\lambda_3 = 1150$ nm | $\theta_3 = 46°$ |
|---|---|---|
| $\Delta LC_2 = 90°$ | $\lambda_3 = 1050$ nm | $\theta_3 = -5°$ |
| $\Delta L = 180°$ | Achromatic | $\theta_2 = 92°$ |
| $\Delta LC_1 = 90°$ | $\lambda_1 = 600$ nm | $\theta_1 = 72°$ |

Figure 8:
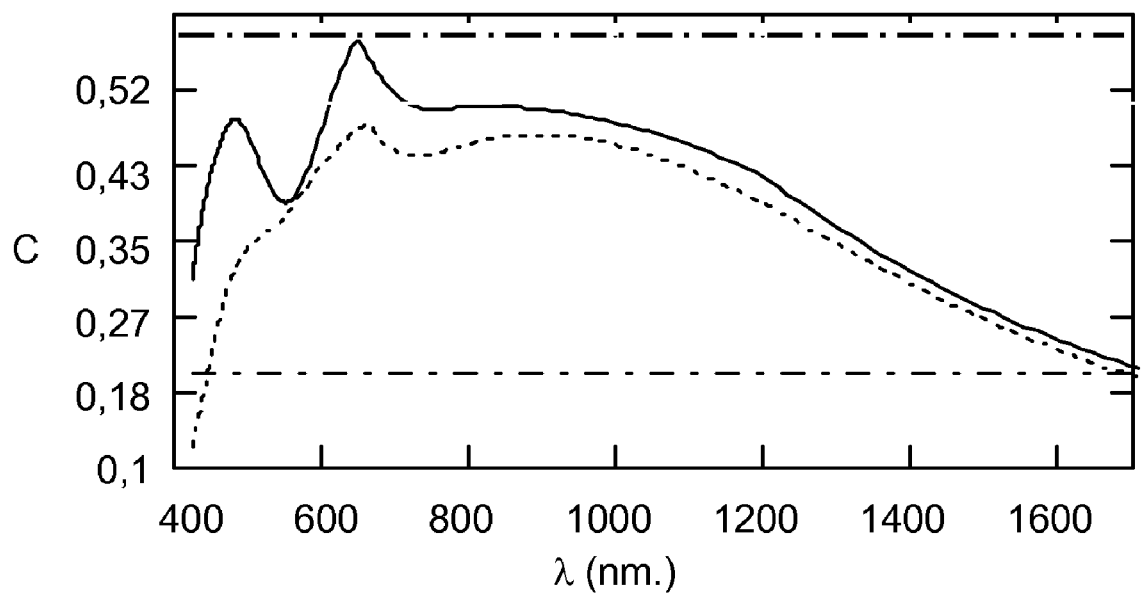
FIG. 8 shows conditioning spectra corresponding respectively to configurations I and III of a polarimeter of the invention.

FIG. 8 shows the conditioning values (continuous black line) for a PGS or a PSA operating in the 400 nm to 1700 nm range when mounted on configuration III using the specifications set out in Table 5. The dashed black line represents the conditioning for a PSG or a PSA operating in configuration III with the specifications of Table 5 but without the achromatic plate. The achromatic plate serves to improve the conditioning, in particular in the visible range.

In a variant of the second embodiment of the invention, referred to as configuration IV, the polarimeter is identical to the above-described polarimeter of configuration III, but it operates in reduced mode. This polarimeter has three ferroelectric devices and a fixed delay plate 4 (that is preferably as achromatic as possible) in the PSG, and another achromatic plate 14 in the PSA. Nevertheless, a reduced sequence of six polarization states is generated (instead of a sequence of eight states as in configuration III), and a reduced sequence of six polarization states is analyzed so that a reduced sequence of thirty-six acquisitions is measured.

The parameters relating to the delays and the relative orientations of the liquid crystal devices 1, 2, and 3 in a PSG (and the devices 11, 12, and 13 in a PSA) that serve to optimize conditioning spectrally are given in Table 6. The states used here are the states Nos. 1, 2, 3, 6, 7, and 8 as shown in Table 2.

TABLE 6

Optimized values for the orientations of three FLCs
of a PSG or a PSA in config. IV operating in reduced mode

| $\Delta LC_3 = 90°$ | $\lambda_3 = 1130$ nm | $\theta_3 = 28.6°$ |
|---|---|---|
| $\Delta LC_2 = 90°$ | $\lambda_3 = 1060$ nm | $\theta_3 = 15.6°$ |
| $\Delta L = 180°$ | Achromatic | $\theta_2 = -14.4°$ |
| $\Delta LC_1 = 90°$ | $\lambda_1 = 578$ nm | $\theta_1 = -28°$ |

Figure 9:
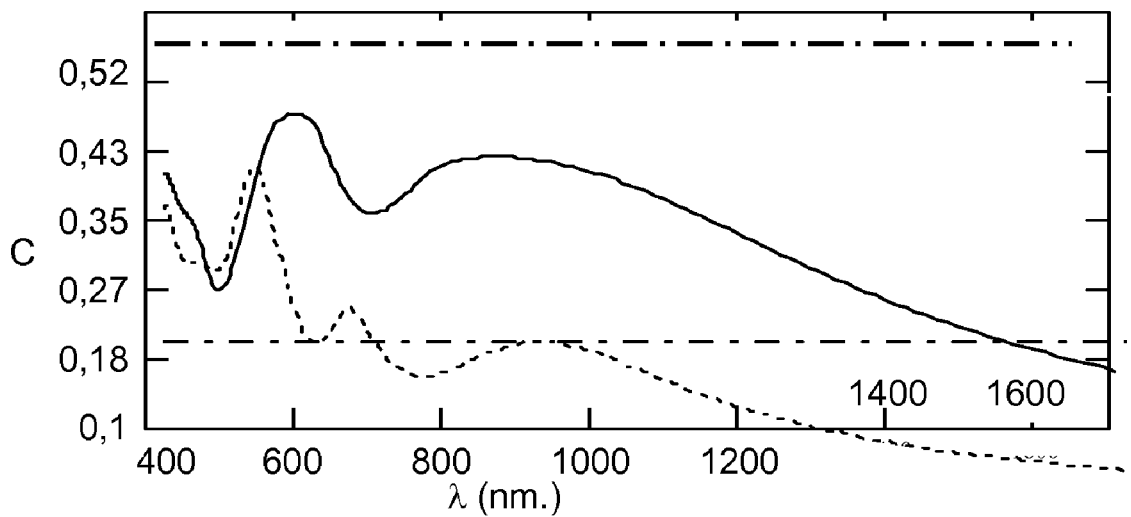
FIG. 9 shows conditioning spectra corresponding respectively to configurations II and IV of a polarimeter of the invention.

FIG. 9 shows two curves. The continuous black curve represents conditioning values for a PSG or a PSA operating in configuration IV (reduced mode) with the optimum values set out in Table 6. The omission of the achromatic plate from the setup would result in the conditioning values represented by the dashed line curve. It can be seen that there is a considerable degradation in the conditioning curve when there is no achromatic plate. The achromatic plate serves to improve conditioning, in particular in the red and near infrared range of 650 nm to 1700 nm.

Configuration IV is insensitive to variations in the delay of FLC1 and of the achromatic plate. The tolerance for drift in the delay of the crystals FLC3 and FLC4 is about ±4°.

The four embodiments described above all relate to polarimeters based on ferroelectric liquid crystal cells. The invention is not limited to cells of that type. In the following examples, a polarimeter is described that is based on using nematic liquid crystal cells.

Figure 5:
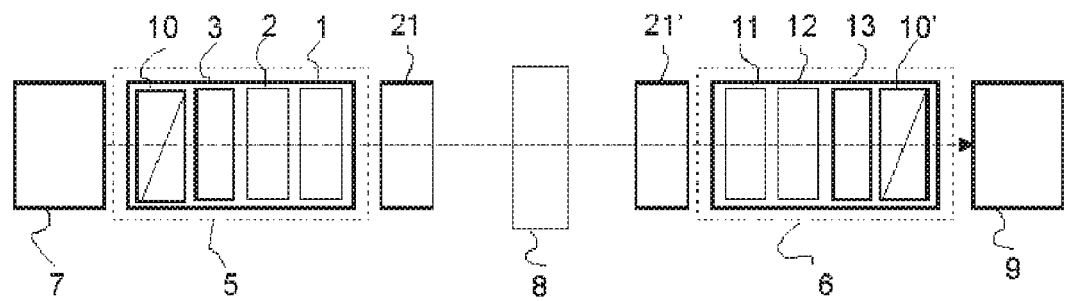
FIG. 5 is a diagram of a third embodiment (types V or VI) of a polarimeter of the invention.

In a third embodiment of the invention (complete mode, configuration V, and reduced mode, configuration VI), shown diagrammatically in FIG. 5, the polarimeter has a PSG 5 with three nematic liquid crystal cells 1, 2, and 3, and a PSA 6 comprising three nematic liquid crystal cells 11, 12, and 13.

In configuration V, the voltage applied to the terminals of the nematic cells 1, 2, and 3 is modulated between two values ($V_A$ and $V_B$). The orientation of the nematic cells remains stationary, but their phase shift varies as a function of the values of $V_A$ and $V_B$. When operating in complete mode, the PSA 5 can thus generate a sequence of eight polarization states, as can the PSA 6. The phase shift values and the orientations of the cells that optimizing conditioning for the PSG 5 and for the PSA 6 in the broadest possible spectral range are given in Table 7:

TABLE 7

Optimized values for phase shifts and orientations of the three nematic liquid crystal cells of a PSG or a PSA in configuration V (complete mode)

| | | | |
|---|---|---|---|
| $\Delta A_3 = 95°$ | $\Delta B_3 = 245°$ | $\lambda_3 = 640$ nm | $\theta_3 = 65°$ |
| $\Delta A_2 = 50°$ | $\Delta B_2 = 158°$ | $\lambda_2 = 780$ nm | $\theta_2 = -70°$ |
| $\Delta A_1 = 10°$ | $\Delta B_1 = 225°$ | $\lambda_1 = 850$ nm | $\theta_1 = 38°$ |

Figure 10:
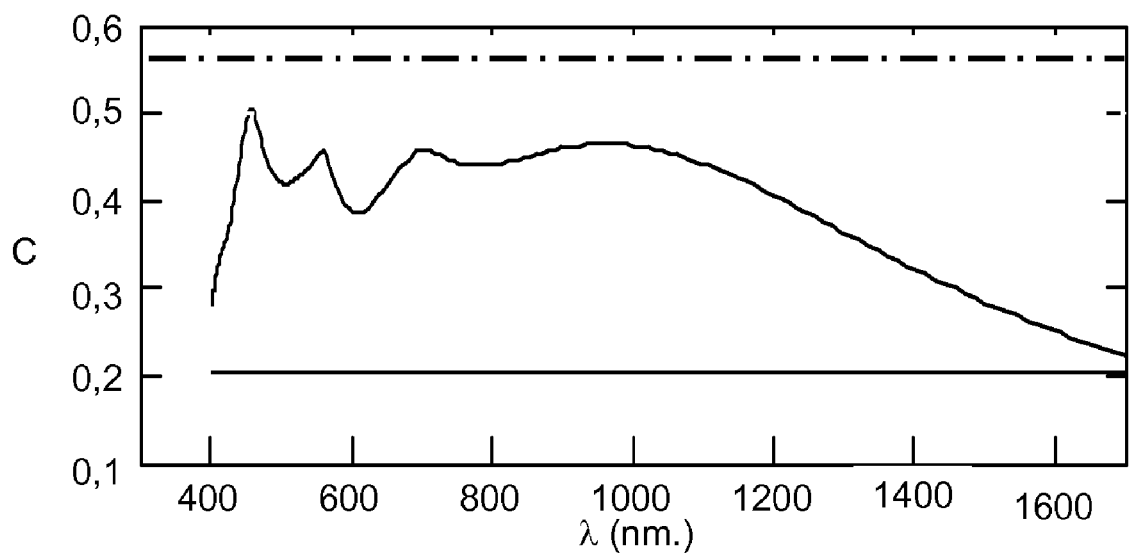
FIG. 10 shows a conditioning spectrum corresponding to a polarimeter of the invention in a type V configuration.

FIG. 10 shows the conditioning spectral values for the values of Table 7, i.e. for a complete sequence of 64 acquisitions. The conditioning values that are obtained in this way are remarkably high (close to the theoretical maximum) over a broad spectral range of 450 nm to 1100 nm, and they are very uniform.

In addition, this embodiment having three NLCs when used with a complete sequence of 64 acquisitions is relatively insensitive to the alignment and to variations in the delays of the crystals. Tolerance on the orientation angle for NLC2 is ±9°, and for NLC1 and NLC3 the tolerance is as much as ±20°.

Configuration VI corresponds to a polarimeter having three nematic liquid crystal devices in the PSG, and three nematic liquid crystal devices in the PSA. Each of the PSG and the PSA generates a sequence of six polarization states, thereby bringing the number of acquisitions needed to take a measurement in reduced mode to 6×6=36.

The voltages applied to the terminals of the nematic liquid crystal devices 1, 2, and 3 of the PSG 5, and of the nematic liquid crystal devices 11, 12, and 13 of the PSA 6 are modulated between two values ($V_A$, $V_B$). The orientations of the nematic cells remains stationary, but their phase shifts vary as a function of the values $V_A$ and $V_B$.

In this example, it is chosen to use the following sequence of polarization states: Nos. 1, 2, 3, 6, 7, and 8, as shown in Table 2.

The values of the phase shifts and also the orientations of the cells that optimize the conditioning of the PSG 5 and of the PSA 6 in the broadest possible spectral range are given in Table 8.

TABLE 8

Optimized values for phase shifts and orientations of the three nematic liquid crystal cells of a PSG or a PSA in configuration VI (reduced mode)

| | | | |
|---|---|---|---|
| $\Delta A_3 = 70°$ | $\Delta B_3 = 225°$ | $\lambda_3 = 520$ nm | $\theta_3 = 70°$ |
| $\Delta A_2 = 15°$ | $\Delta B_2 = 170°$ | $\lambda_2 = 650$ nm | $\theta_2 = -70°$ |
| $\Delta A_1 = 42°$ | $\Delta B_1 = 280°$ | $\lambda_1 = 750$ nm | $\theta_1 = 35°$ |

Figure 11:
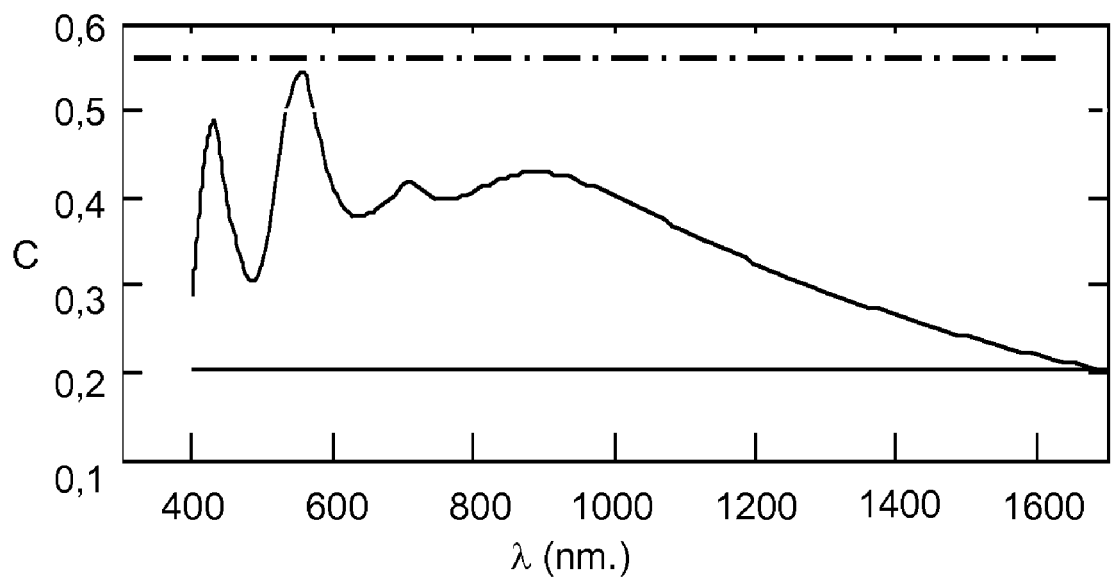
FIG. 11 shows a conditioning spectrum corresponding to a polarimeter of the invention in a type VI configuration.

FIG. 11 shows the conditioning spectral values for the values of Table 8, i.e. for a reduced sequence of 36 acquisitions. The conditioning obtained in this way is good, but not as good as for complete mode with 64 acquisitions. Nevertheless, measurement lasts for half as long as in complete mode. Sensitivity to alignment defects of the liquid crystal cells and also to delay drift of the cells is approximately doubled in reduced mode compared with a measurement comprising a complete sequence of 64 acquisition. Tolerance on the angle of orientation of NLC2 is ±4.5°, and for NLC1 and NLC3 this tolerance is ±10°.

FIGS. 12 and 13 are simulations of Mueller matrices for illustrating measurements representative of a polarimeter of the present invention. The two matrices correspond to systems commonly encountered when working with thin-film semiconductor materials, as in widespread use in microelectronics and also for photovoltaic energy production. These samples show clearly the advantages of a polarimeter of the invention in comparison with prior art polarimeters. To construct devices based on thin-film semiconductor materials, it is necessary to inspect the thicknesses of those layers. To do that it is necessary to measure samples in a range of wavelengths for which the material forming the layers is transparent. This can readily be understood by considering a sample made up of a stack of layers on a substrate. If one of the layers of the stack is opaque, it does not enable information to be obtained about the layers beneath it since light does not reach them. An explanation that is more complete and more rigorous is to be found in several works, such as for example [Azzam & Baschara, Ellipsometry and polarized light, North Holland, 1987]. For materials based on silicon, which are the materials presently in the most widespread use, such as amorphous silicon, monocrystalline silicon, or polycrystalline silicon, it is found that their transparency range lies at wavelengths longer than 730 nm, 960 nm, and 950 nm, respectively. This implies that the prior art polarimeters having a working spectral range limited at best to 400 nm to 900 nm are not suitable. The use of polarimeters working at longer wavelengths, in the near infrared, is clearly better. Measuring thicknesses of thin layers by spectroscopic methods is made easier by the appearance of interference fringes in the measured spectra. These interference fringes are visible only for spectral ranges in which the layers are transparent or only slightly absorbent. The positions and the number of such interferences fringes depend on the refractive indices of the materials constituting the layers and also on their thicknesses [Azzam & Baschara, Ellipsometry and polarized light, North Holland, 1987]. The number of these interference fringes increases in proportion with the thicknesses of the layers and inversely with the measurement wavelength. Consequently, it is advantageous to use the longest possible wavelengths. In order to be able to make use of interference phenomena for metrological purposes, it is necessary to be capable of measuring interference using apparatus that is capable of resolving interference while avoiding phenomena of "aliasing" or under-sampling. In practice, samples based on semiconductor materials use layers or multilayers in which the sum of the thicknesses exceeds or is of the order of one micrometer. Under such conditions, in the transparent spectral range of the thin layers that is accessible to prior art polarimeters, the fringes that are observed are too few and much too close together to enable them to be properly measured. This limits the usefulness of those apparatuses and consequently represents a drawback. Having a polarimeter capable of making measurements in the near infrared enables the number of measured fringes to be increased and also makes it possible to avoid the phenomenon of under-sampling by using wavelengths that are much longer.

FIG. 12 represents the Mueller matrix for a pair of layers comprising a 1 micrometer thick layer of polycrystalline silicon and a 100 nm thick amorphous layer deposited on a monocrystalline silicon substrate having a thickness of 0.5 mm. This pair of layers is quite representative since it is to be found in the stacks used for fabricating microelectronic transistors. Since the sample is isotropic, the Mueller matrix presents a certain degree of symmetry. The elements of the matrix belonging to non-diagonal blocks are zero. The elements [1,2] and [2,1] are equal, the elements [3,3] and [4,4] are equal, and the elements [3,4] and [4,3] are of equal magnitude and opposite signs. In the visible range going from 400 nm to 700 nm, there can be seen a strip with very small fringes due to the amorphous silicon, while in the near infrared, from 1000 nm to 1700 nm, there can be seen four fringes that indicate the presence of the layer of polycrystalline silicon, which layer is also thicker. The polarimeter of the invention thus makes it possible to obtain a measurement concerning the layer of polycrystalline silicon over a very broad spectral range, which is not possible using a polarimeter that is limited to the visible range.

FIG. 13 also shows a system that is quite common in the fabrication of solar photovoltaic cells or flat screens. It comprises depositing a thickness of about 2 micrometers of amorphous silicon on a glass substrate having a thickness of 0.5 millimeters. Since the sample is isotropic, its Mueller matrix presents the symmetries as for the example shown in FIG. 12. The simulated data resolution is 3 nm, which is identical to that of prior art polarimeters. In the 500 nm to 800 nm range, a much greater number of fringes appear that are very close together and not fully resolved, thereby revealing a phenomenon of under-sampling. However, in the near infrared, and for the reasons explained above, the fringes spread out and they can be resolved completely. In this second application, measurement over a broad spectral range including the near infrared is also a major advantage compared with the limitations of prior apparatuses in the visible range.

The polarimeter of the invention makes it possible with a single apparatus to perform spectroscopic measurements covering a very broad spectral range with very good uniform conditioning throughout the range.

In the invention, the PSG generates more than four different Stokes vectors, and is represented in the form of a 4×m matrix where m is an integer greater than 4, and the PSA determines more than four different Stokes vectors on output. The matrix A is represented in the form of an n×4 matrix where n is an integer greater than 4. In a preferred embodiment of the invention, the polarization modulation means suitable for generating the Stokes vectors of the PSG and the PSA are liquid crystal devices. In a preferred embodiment of the invention, the liquid crystal devices are ferroelectric crystal cells, there being three in the PSG and in the PSA.

The PSG is thus suitable for generating eight polarization states, and the PSA is suitable for determining eight polarization states. The polarimetric system is thus capable of making 64 acquisitions. These 64 measurement are not independent, but it is specifically their redundancy that makes it possible to improve the quality criterion of the calibration over an extended spectral range.

In the measurement method of the invention, new polarization states are added. 64 measurements are over-determined at one wavelength, but they may be necessary for a spectrum. A search is thus made for states that contribute to improving conditioning at certain wavelengths, which search does not harm conditioning at other wavelengths.

In order to avoid excessively lengthening the time required to acquire a spectrum, it is possible, for example, to remove two states, since their contribution to improving conditioning is not essential.

The polarimeter of the invention may be optimized so that its operation is at an optimum over a broad spectral range. The optimization criterion consists in maximizing the conditioning of the matrices that represent the PSG and the PSA and in making the conditioning as uniform as possible in the measurement spectral range.

The duration of a measurement depends on the number of polarization states used. When using a complete sequence of 64 polarization states, the duration of measurement is increased by a factor of four compared with a measurement formed on a sequence of 16 polarization states, as used in prior art polarimeters. Nevertheless, the duration of measurements need be increased by a factor of no more than ≈2 relative to a conventional measurement, if a reduced sequence of only 36 states is used.

The spectroscopic polarimeter/ellipsometer of the invention serves to cover a spectral range that is much broader than prior devices by generating and/or analyzing a larger number of polarization states.

The invention also provides a method of measurement acquisition for a polarimeter that makes it possible to perform accurate spectroscopic measurements over a broad spectral range with accuracy being uniform over the range.

The invention claimed is:

1. A spectroscopic polarimetric system for analyzing a sample (8), the system comprising:
    an excitation portion comprising:
        a light source (7) suitable for emitting an incident light beam (17) over a wavelength range; and
        a polarization state generator (PSG) (5) comprising:
            a linear polarizer (10) and means for modulating the polarization of the light beam;
    an analyzer portion comprising:
        a polarization state analyzer (PSA) (6) comprising:
            means for modulating the polarization of the light beam and a linear polarizer (10'); and
            detector means (9) for detecting the light beam as a function of wavelength and including a processor unit;
    the system being characterized in that:
    the means for modulating the polarization of the PSG (5) comprise three liquid crystal devices (1, 2, 3) and voltage control means applied to each of the liquid crystal devices (1, 2, 3) suitable for modulating the orientation and/or the delay of the polarization states so as to generate a sequence of m polarization states with m>4 at each measurement wavelength;
    the means for modulating the polarization of the PSA (6) comprise three liquid crystal devices (1, 2, 3) and voltage control means applied to each of the liquid crystal devices (1, 2, 3) suitable for modulating the orientation and/or the delay of the polarization states so as to determine a sequence of n polarization states with n>4 at each measurement wavelength; and the detector means are suitable for acquiring a sequence of N light intensity measurements where:

$16 < N \leq n \times m$ at each wavelength to extract the Mueller matrix of the sample (8) therefrom.

2. A polarimetric system according to claim 1, characterized in that the excitation portion includes a retractable platform (21) situated between the PSG (5) and the sample (8) and suitable for introducing at least one calibration element in the optical system of the polarimetric system and for withdrawing said calibration element once calibration has been terminated, and the analyzer portion includes a retractable platform (21') situated between the PSA (6) and the sample (8) and suitable for introducing at least one calibration element in the optical system and for withdrawing said calibration element once calibration has been terminated.

3. A polarimetric system according to claim 1, characterized in that the means for modulating the polarization of the PSG are suitable for generating a sequence of m=8 polarization states at each measurement wavelength, the means for modulating polarization of the PSA are suitable for determining a sequence of n=8 polarization states at each measurement wavelength, and the detector means are suitable for acquiring a sequence of N=64 measurements at each wavelength to extract the Mueller matrix of the sample (8) therefrom.

4. A polarimetric system according to claim 1, characterized in that the means for modulating the polarization of the PSG are suitable for generating a sequence of m=6 polarization states at each measurement wavelength, the means for modulating the polarization of the PSA are suitable for determining a sequence of n=6 polarization states at each measurement wavelength, and the detector means are suitable for acquiring a sequence of N=36 measurements at each wavelength to extract the Mueller matrix of the sample (8) therefrom.

5. A polarimetric system according to claim 1, characterized in that the means for modulating the polarization of the PSG comprise three ferroelectric liquid crystal (FLC) devices (1, 2, 3) suitable for generating a sequence of m=8 polarization states, and in that the means for modulating the polarization of the PSA comprise three FLC devices (11, 12, 13) suitable for determining a sequence of n=8 polarization states.

6. A polarimetric system according to claim 5, characterized in that the polarization state generator (5) includes a delay plate (4) located between two of the FLCs (1, 2) or (3, 2), and in that the polarization state analyzer (6) includes a delay plate (14) located between two FLC devices (11, 12) or (12, 13).

7. A polarimetric system according to claim 6, characterized in that the delay plates (4, 14) are achromatic double prisms.

8. A polarimetric system according to claim 1, characterized in that the liquid crystal cells (1, 2, 3, 11, 12, 13) are nematic liquid crystal cells and in that the polarimetric system includes an electronic control device suitable for modulating the delays of the nematic liquid crystal cells (1, 2, 3, 11, 12, 13).

9. A polarimetric system according to claim 8, characterized in that the means for modulating the polarization respectively of the PSG and of the PSA comprise respectively three nematic liquid crystal (NLC) devices (1, 2, 3) and (11, 12, 13), and in that voltage control means are suitable for switching the delay of each NLC device (1, 2, 3, 11, 12, 13) in such a manner as to generate a sequence of m=8 polarization states and respectively to determine a sequence of n=8 polarization states.

10. A polarimetric system according to claim 1, characterized in that the polarimetric system is optimized for the spectral range 350 nm to 2 µm.

11. A polarimetric system according to claim 1, wherein the polarimetric system is an ellipsometer.

12. A polarimetric system according to claim 1, wherein the polarimetric system is a Mueller polarimeter for analyzing a sample (8) from a sequence of N detected light intensity measurements where $16 < N \leq 64$.

13. A polarimetric system according to claim 1, characterized in that the detector means (9) comprise an imaging detector adapted to the processor unit to form a polarimetric image of the sample (8).

14. A method of spectroscopic polarimetric measurement of a sample (8), the method comprising the following steps:
    illuminating the sample (8) by means of a polarized incident light beam (17) emitted by a polarization state generator (PSG) (5) including a polarizer, said PSG modulating the polarization state of the light beam (17), said sample (8) transmitting or reflecting the polarization modulated light beam;
    detecting the measurement by means of a detector and a detection section comprising a polarization state analyzer (PSA) (6) and a polarizer, said PSA determining the polarization state of the detected light beam; and
    processing the detected signals in order to extract a polarimetric measurement of the sample therefrom;
    the method being characterized in that the polarization states generated by three liquid crystal devices (1, 2, 3) are modulated in a sequence of m>4 polarization states, the polarization states analyzed by three liquid crystal devices (11, 12, 13) are determined in a sequence of n>4 polarization states, and a sequence of N=n×m measurements.

15. A spectroscopic polarimetric measurement method according to claim 14, characterized in that a sequence of eight polarization states is generated, a sequence of eight polarization states is analyzed, and a sequence of 64 measurements is acquired at each wavelength.

16. A spectroscopic polarimetric measurement method according to claim 14, characterized in that a sequence of six polarization states is generated, a sequence of six polarization states is analyzed, and a sequence of 36 measurements is acquired at each wavelength.

17. A polarimetric system according to claim 2, characterized in that the means for modulating the polarization of the PSG are suitable for generating a sequence of m=8 polarization states at each measurement wavelength, the means for modulating polarization of the PSA are suitable for determining a sequence of n=8 polarization states at each measurement wavelength, and the detector means are suitable for acquiring a sequence of N=64 measurements at each wavelength to extract the Mueller matrix of the sample (8) therefrom.

18. A polarimetric system according to claim 2, characterized in that the means for modulating the polarization of the PSG are suitable for generating a sequence of m=6 polarization states at each measurement wavelength, the means for modulating the polarization of the PSA are suitable for determining a sequence of n=6 polarization states at each measurement wavelength, and the detector means are suitable for acquiring a sequence of N=36 measurements at each wavelength to extract the Mueller matrix of the sample (8) therefrom.

* * * * *